United States Patent [19]
Parasher

[11] Patent Number: 5,535,756
[45] Date of Patent: Jul. 16, 1996

[54] CATHETER WITH SIMULTANEOUS BRUSH CYTOLOGY AND SCRAPE BIOPSY CAPABILITY

[76] Inventor: Vinod K. Parasher, Long Neck Rd.-Suite #1, Millsboro, Del. 19966

[21] Appl. No.: 178,112

[22] Filed: Jan. 6, 1994

[51] Int. Cl.⁶ .................................................. A61B 10/00
[52] U.S. Cl. ........................................................ 128/756
[58] Field of Search ............................... 128/749, 756, 128/759, 657, 658, 772; 606/191, 194, 196

[56] References Cited

U.S. PATENT DOCUMENTS

| | | | |
|---|---|---|---|
| 3,196,876 | 7/1965 | Miller | 606/191 |
| 4,465,072 | 8/1984 | Taheri | 128/756 |
| 4,726,373 | 2/1988 | Greengrass | 606/191 |
| 5,201,323 | 4/1993 | Vermeulen | 128/756 |

FOREIGN PATENT DOCUMENTS

| | | | |
|---|---|---|---|
| 1547328 | 6/1979 | United Kingdom | 128/756 |

*Primary Examiner*—Max Hindenburg
*Attorney, Agent, or Firm*—Eckert Seamans Cherin & Mellott

[57] ABSTRACT

A medical device performs simultaneous brush cytology and scrape biopsy on structures within an organic duct by collecting cells and tissue on a brush having irregular semi-rigid bristles, preferably formed as the hook portion of a hook and pile fastener (e.g., the hook portion of a Velcro pad). A wire guided catheter has a brush strip located near a distal end for insertion into the duct. Once the distal end and brush are positioned at a selected location within the duct, the catheter is pushed and pulled back and forth to gather cells and scrapings from the selected location, which accumulate in the irregular bristles. The catheter can be enclosed in a retractable sleeve during insertion and/or withdrawal. An enlargement at the distal end of the catheter assists in opening the duct to admit the brush. A radio-opaque marker is externally detectable to assist in locating the brush at the selected location. The relatively stiff irregular bristles improve the extent to which cells and tissues can be collected and permit collection of enough tissue to provide a biopsy sample, without substantial risk of perforation of the duct.

15 Claims, 2 Drawing Sheets

CATHETER WITH SIMULTANEOUS BRUSH CYTOLOGY AND SCRAPE BIOPSY CAPABILITY

BACKGROUND OF THE INVENTION

1. Field of the Invention

This invention relates to devices for collecting cell samples from internal organs, and in particular to a catheter capable of simultaneously performing brush cytology and scrape biopsies of structures within biological ducts, employing a polymeric hook pad with relatively stiff irregularly shaped bristles for collecting cells from a sample site. More particularly, a wire guided catheter having a hook pad of a hook and pile fastener (e.g., Velcro) at its distal end is used for abrading against the duct walls to collect cells and tissue.

2. Description of the Prior Art

It is sometimes necessary to collect a sampling of cells from internal organs, typically using an endoscope or laparoscope to obtain access to the site to be sampled, for laboratory analysis in connection with a diagnosis. In connection with certain bodily ducts, a tumor in the tissue of the duct or in tissues adjacent the duct may present as a narrowing or stricture of the duct at a localized area. Cancer of the bile duct or the pancreatic ducts, for example, present as a narrowing or stricture. Similarly, strictures can be seen in the esophagus, the stomach, the colon, and other duct-like organs. It is useful in connection with diagnosis to examine the cells at a stricture to better assess its cause.

Known cytological techniques for collection of cell samples at duct strictures and other sites have a number of shortcomings. The diagnosis of pancreato-biliary malignancy is an example. Normally, an endoscope is used to obtain access to the collection site, for example the pancreatic duct leading from the pancreas to the duodenum. A cell collection tool that is basically an elongated brush usually having soft bristles set in twisted strands of wire is passed through the endoscope. Using the wire to pull the brush in opposite directions, the bristles are brushed over the inner wall of the duct at the stricture, in an effort to displace cells from the duct wall and capture the cells in the bristles. This technique is sometimes called "brush cytology" or just "cytology."

The brush can be placed in a sleeve to assist in guidance to the sample site, to avoid picking up cells from areas other than the stricture, and to protect the sample after it is collected. The sleeve can have one or more radio-opaque marks to help in placing the brush at the stricture. More particularly, fluoroscopy is used to visualize the location of the sleeve by the radio-opaque mark and therefore to assist in placing the brush in the stricture.

Unfortunately, brush cytology as described is only adequate to collect sufficient cells to effect diagnosis in about 18 to 70% of attempts. The technique offers no biopsy capability because it cannot effectively extract a gross tissue sample from the area of the stricture. Diagnosis of a potential malignancy, however, certainly requires dependable results in the collection of cells, and may require collection of a more extensive biopsy sample. To diagnose a malignancy associated with a stricture, for example, it may be appropriate to examine the mucous lining of the duct, the tissue of the duct wall and even adjacent tissues. The known brush cannot extract sufficient cells and tissue in a dependable manner. The known wire-carried brush can be reciprocated using the wire but it is not guided by the wire. Accordingly, the known brush is difficult to use effectively in difficult to reach, narrow areas of the ducts. Presently, a biopsy of the area of the stricture is obtained by passing a different instrument, typically a biopsy forceps, through the endoscope and then cutting away and removing a relatively large chunk of the tissue from the diseased area. However, use of biopsy forceps involves an inherent risk of perforating the duct, and for this reason their use is not preferred.

SUMMARY OF THE INVENTION

It is an object of the invention to provide a method and apparatus that can better collect a tissue sample from a stricture in a duct or from another anatomical structure, preferably that can obtain a sufficient sampling of cells to assist in diagnosis more dependably. More particularly, there is a need to enable collection of a sample sufficient to qualify as a biopsy, but in a manner that reduces the risk of perforating the duct as compared with known techniques.

It would be advantageous therefore to provide an instrument that is capable of obtaining a brush cytology sample that can also be used to obtain a larger tissue sample for a biopsy, preferably enabling selection of a brush sample more dependably, and enabling collection of a gross tissue sample or biopsy, using the same tool and substantially via the same procedure. Such an instrument would be particularly useful in the diagnosis of anomalies of the pancreato-biliary structures, such as a malignancy presented as a stricture of the ducts.

These and other objects are met according to the invention in a device capable of performing a brushing of tissue at a stricture in a duct for collecting cells (cytology) and also capable of obtaining a greater sample of the tissue (biopsy) at the stricture in a procedure that combines cytology and biopsy. The duct can be, for example, the common bile duct, the pancreatic duct, and any of a number of other duct-like organs and the like, such as, for example, the esophagus, the stomach, the large bowel, the lungs, the uterus, the ureter, the kidney, etc., all such organs being collectively referred to herein as ducts.

The device includes an elongated, flexible catheter and a brush made of semi-rigid bristles with irregular shapes for capturing cells and tissue in the bristles, preferably bristles on a pad or fabric of the type conventionally used as the hook side of hook and pile fasteners such as Velcro. The brush is located adjacent a distal end of the catheter. The catheter is inserted into the duct or duct-like organ, and can be passed over a guide wire for guiding the catheter into and through the duct.

According to another aspect of the invention, the bristles of the brush provide an inherent structure for capturing and then protecting the collected cells. Accordingly, the individual bristles can include hooks, ball-shaped, looped, mushroom-shaped or T-shaped structures at their ends, tending to collect cells and tissue and to retain the collected material during withdrawal of the device. The hooks can be separately formed or provided as cut loops, or formed in another manner known in connection with use of the bristles as fastener elements.

According to another aspect, the distal end of the catheter that is inserted into the duct can be ball-tipped with a radio-opaque ball, or structured for expanding the duct to allow the brush to pass through the duct as the bristles work on the inner wall of the duct.

The catheter can include a marking device located adjacent to the brush, such as a radio-opaque mark, to assist in guiding the catheter to a desired location in the duct, as viewed fluoroscopically. Additionally, a retractable sleeve can be provided to encompass the brush during passage of the catheter to a selected location in the duct, and/or to protect the collected sample when being removed on the brush.

The invention includes a method for performing combined cytology and biopsy in a duct using a wire-guided catheter as described. The brush near the distal end of the catheter that is to be inserted into the duct is fabricated of semi-rigid irregularly shaped bristles, e.g., hooked or blunt ended bristles or the like, for example the bristles of a hook pad material such as Velcro. The method includes the steps of first performing endoscopy to obtain access to an opening into the respective duct. For example, in a bile duct or a pancreatic procedure, an endoscopic retrograde cholangio pancreatography (ERCP) is performed. The endoscope can be brought near to the site of to be sampled, such as a stricture, if this is convenient. A blunt-ended guide wire is moved into the duct so as to pass a selected area of the duct at which the cytology is to be performed and/or a biopsy sample taken. The distal end of the catheter, including the brush, is then inserted over the guide wire into the duct, i.e., with the wire passing through the lumen of the catheter. The brush bearing end of the catheter is moved to the selected area of the duct and pushed and pulled, back and forth over the inner wall of the duct. The bristles of the brush collect sample scrapings of tissue and brushings of cells at the selected area. The end of the catheter with the brush is withdrawn from the duct through the endoscope or into a sleeve provided to protect the sample. The scrapings of tissue and cells that cling to the brush can then be removed and analyzed by standard methods.

According to a further aspect of the invention, the catheter can include markers, such as radio-opaque markers, located near the brush and for example straddling the brush along the longitudinal axis of the catheter, for assisting in guiding the brush to the selected area. According to another aspect of the invention, the first end of the catheter includes an expansion mechanism for expanding the duct. The method includes the further step of expanding a section of the duct with the expansion mechanism before passing the brush into the selected area. This can be especially useful in the case where the selected area has a very narrow stricture.

According to another aspect of the invention, a longitudinally retractable sheath, or sleeve made of nylon, polyethylene, polyurethane, polytetrafluoroethylene (Teflon) or the like, covers the brush as it is guided to the selected area. The sheath is retractable in a telescoping manner to expose the brush at the selected area before the brush is pushed and pulled over the tissues, and after brushing the sleeve can be moved back over the brush, or the brush can be withdrawn into the sleeve. Thus the brush can be deployed internally, used and then protected against loss or contamination of the sample, before removing the brush from the duct.

The catheter and the brush thereon can be withdrawn along the guide wire. After removing the catheter from the duct, a stent can be passed over the guide wire in place of the catheter, for keeping the duct open through the area of the stricture. The guide wire can then be withdrawn.

Cytology can be rendered more effective according to the invention because a more substantial sample can be taken than with the brush apparatus conventionally known. The brush can be operated more gently for collection of cells or more vigorously to obtain pieces of tissue for biopsy analysis. Nevertheless, the brushing procedure is safer than surgical extraction of tissue from the wall of the duct.

These and other objects of the invention will be more fully understood from the following description of the invention with reference to the accompanying drawings.

DETAILED DESCRIPTION OF THE PREFERRED EMBODIMENTS

Figure 1:
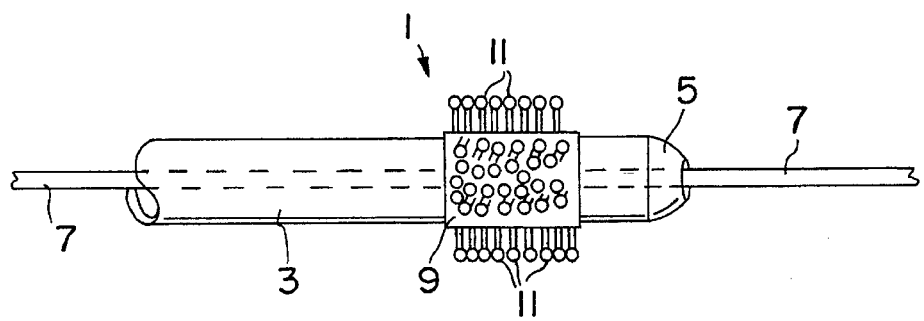
FIG. 1 is a partial elevation view of a first embodiment of the device of this invention.

A first embodiment of a device 1 according to the invention is illustrated in FIGURE. 1. Device 1 includes a flexible, hollow tube 3, or catheter, having a ball tip 5, for example of metal. Similar structures of the respective embodiments will be referenced by the same reference numbers throughout this specification for simplicity of exposition. For applications such as taking simultaneous brushings and biopsies of structures in the common bile duct and the pancreatic duct, tube 3 can be, for example, 2 m long and 0.2 cm in internal diameter, such as a No. 6 French nylon catheter, or larger or smaller, as required.

A blunt ended guide wire 7 is placed in the duct to be examined, such that the wire extends beyond the stricture or other site to be sampled. Guide wire 7 can be, for example, a 0.035 inch (0.09 cm) diameter, blunt-ended guide wire, preferably made of a resilient metal, such as steel or titanium coated with an outer layer of a material that is nonreactive, such as polytetrafluoroethylene (Teflon). A metal ball tip 5 on the catheter can be provided both to push aside duct tissues without puncturing them and to provide a radio-opaque structure that can be used to locate the end of the catheter, by fluoroscopy. Alternatively, the tip 5 can be a relatively wider loop end. The catheter is slid over the guide wire to the sampling site.

Catheter 3 comprises a brush 9, preferably arranged around the catheter adjacent the distal end, but also potentially along one lateral side only. Brush 9 comprises a plurality of radially extending, semi-rigid bristles 11 that protrude from a base strip that is attached adhesively to catheter 3 near the distal end. Individual bristles 11 have enlarged or hooked ends, which in a hook and pile fastener is a means by which the ends engage a pile. However, according to the invention, the relatively stiff bristles and their enlarged or hooked ends readily collect cell and tissue samples and provide a zone radially inwardly of the enlarged or hooked ends where the sampled cells and tissue tend to become trapped.

The brush 9 can be made using the hooked side of a Velcro or other hook and pile type fastener, for example with bristles extending radially about 1 to 3 mm. The length of the brush 9 along the longitudinal length of catheter 3 can vary depending upon the application, but preferably is at least 0.5 cm long. For most applications, it need not be more than about 1.5 cm in length, however, longer length brushes are also included within the scope of this invention, and can be used when it is desirable to collect and perhaps to distinguish among cells and tissue collected over a predetermined length of the duct.

Fastener pads as described generally comprise bristles formed on a base web of plastic or the like. The bristle ends can be formed in a number of ways, such as by melting the ends of standing thermoplastic bristles to provide a ball or mushroom shape or to cause the ends to bend rearwardly, forming hooks. Another technique is to form a loop pile and to cut the loops to provide a hooked bristle and a straight bristle. All such alternatives produce irregular bristles useful for collecting cells and tissue. Other forms of the grasping part of pad fastener materials can be used as well. Preferably, the brush or bristle pad is attached by the base of the pad to the catheter. The base can be attached by adhesive, heat welding or the like to provide a secure connection. The bristle bearing pad can extend part way around the circumference of the catheter, but preferably extends substantially around a full 360°.

Figure 2:
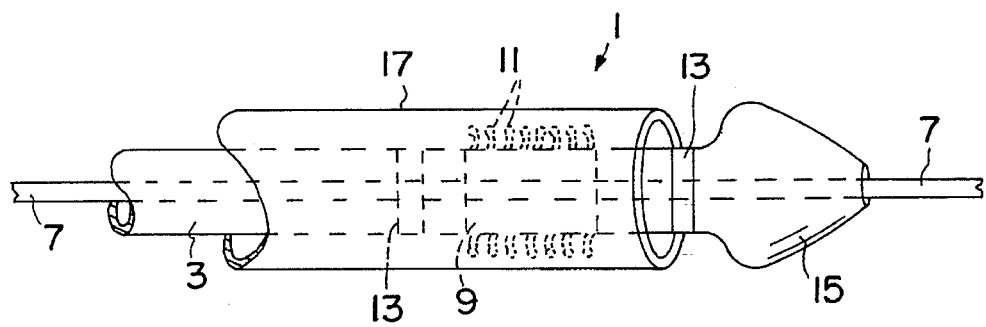
FIG. 2 is a partial elevation view of a second embodiment of the device of this invention.

Referring to FIG. 2, an alternative embodiment of the device includes markers 13, such as metal bands or clips, on one or both longitudinal sides of brush 9 for locating the distal end of the catheter and the brush while in the duct. Markers 13 are visible by fluoroscopy. The embodiment of FIG. 2 also includes a means for dilating the duct with longitudinal advance of catheter 3, for assisting passage through the duct of brush 9. Brush 9 is slightly wider than the portion of catheter 3 where brush 9 is mounted within the duct. The distal end of the catheter 3 as shown has an enlarged, preferably cone-shaped structure 15 in this embodiment to mechanically dilate the duct as the distal end is inserted. Other means, such as inflatable balloon catheter means, can be used as another way to dilate the duct.

Figure 3:
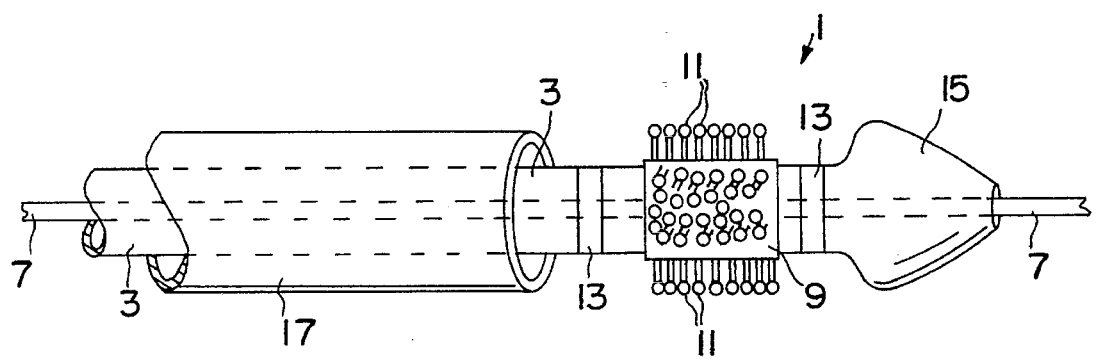
FIG. 3 is a partial elevation view of a third embodiment of the device of this invention, including a retractable sleeve that can be positioned over the bristles of the brush.

Preferably, the device is used with a retractable sheath or sleeve 17, that can be moved longitudinally relative to catheter 3, in particular in both directions between a position covering the brush (as in FIG. 2) and a retracted position exposing the brush (as in FIG. 3). The sleeve 17 likewise can be fabricated of nylon, polyethylene, Teflon or the like. Sleeve 17 just fits over catheter 3, and is effective to prevent brush 9 from picking up cell or tissue samples before being deployed in place at the sample site, and to prevent contact between brush 9 and the duct after the sample is collected, which contact could cause captured cells and tissue to come free of brush 9 or additional cells or tissue to be picked up from other sites.

Figure 4A:
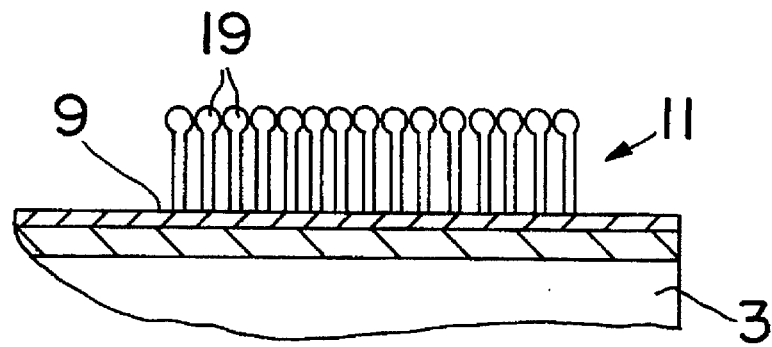
FIG. 4a–4c are elevational views of three preferred embodiments of bristle designs for the brush.
Figure 4B:
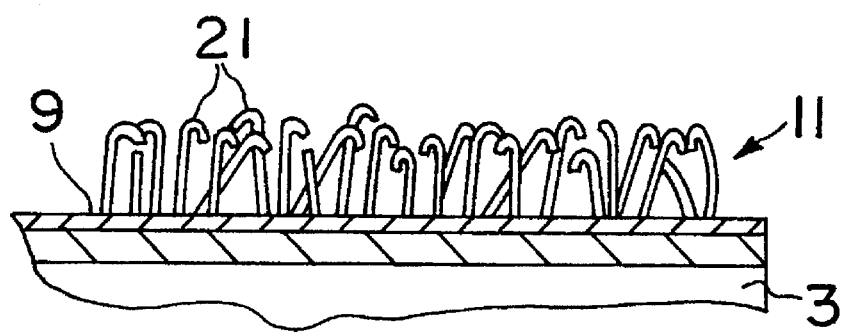
Figure 4C:
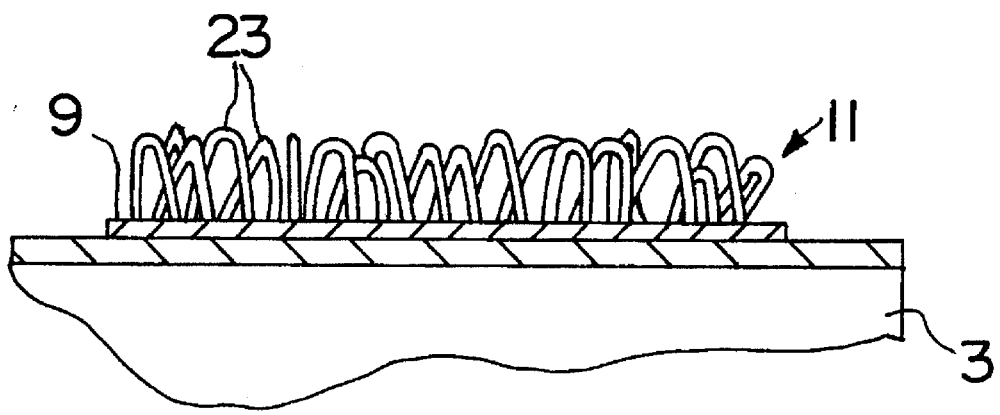

FIGS. 4a–4c illustrate different preferred embodiments for bristles 11 of brush 9. In FIG. 4a bristles 11 have a ball-tip or mushroom tip structure 19 located at the distal end of each bristle 11. Bristles 11 in FIG. 4b have hooks 21 at their ends. FIG. 4c illustrates bristles 11 forming closed loops 23. It is to be understood that although three specific embodiments of bristle designs are described herein, this is not meant to be limiting. Other bristle designs having similar characteristics, and in particular that have a structure effective for capturing and holding cells and tissue, are also encompassed within the scope of the invention.

The device of this invention is used in the following manner in performing a combination of cytology and biopsy of a stricture in a pancreatic duct, for example. An ERCP is performed to gain entry to the duct. The guide wire 7 is then passed into the duct sufficiently to approach or preferably pass a selected area of the duct at which the cytology/biopsy is to be performed. The distal end of catheter 3, including brush 9, is inserted over guide wire 7 into the duct. The position is monitored by viewing the ball-tip 5 or other radiographic marker, such as clips 13, with a fluoroscope. Brush 9 is moved to the selected area of the duct. If the duct stricture is very narrow, a catheter having a mechanism for expanding the duct, such as a cone-shaped end 15, can be used to dilate the duct before entry of the brush 9 into the stricture. The brush 9 on catheter 3 is exposed by retracting the sheath or sleeve 17. Catheter 3 then is pushed and pulled, back and forth, several times such that sample scrapings of tissue and brushings of cells from the stricture cling to bristles 11 of brush 9, more particularly being captured by the bristle structures. Catheter 3 is then retracted into sleeve 17 (or sleeve 17 is advanced) sufficiently to protect brush 9. The catheter is withdrawn from the duct together with sleeve 17, through the endoscope. Guide wire 7 can be withdrawn simultaneously or afterwards.

The scrapings of tissue and cells that cling to bristles 11 of brush 9 can be removed and analyzed for abnormalities according to methods known in the art. Prior to retracting guide wire 7, a stent or tube, also known in the art, can be passed over the guide wire 7 after removal of the catheter 3 and left in the stricture to keep the duct unblocked.

Whereas particular embodiments of the present invention have been described above for purposes of illustration, it will be appreciated by those skilled in the art that numerous variations of the details may be made without departing from the invention as described in the appended claims.

I claim:

1. A device for collecting cells from a duct, comprising:

a catheter forming a hollow tube with a brush located close to a distal end of the catheter, for insertion into the duct, wherein the brush is fabricated of semi-rigid bristles protruding radially from the tube, the bristles having irregular shaped tips whereby the cells are collected in the bristles by scraping the brush over an inner wall of the duct;

an enlargement formed in the catheter adjoining the distal end of the catheter;

wherein the enlargement occupies a position separating the brush from the distal end, and is shaped and arranged for expanding the duct to permit passage of the brush during insertion through the duct and for expanding the duct during withdrawal to permit withdrawing from the duct scraped and collected cells; and, a sleeve movably disposed on the catheter to cover and uncover the brush;

wherein the sleeve is formed to be abuttable against the enlargement of the catheter for protecting the scraped cells collected on the brush during withdrawal of the catheter and sleeve combination from the duct.

2. The device of claim 1, wherein the bristles have hooked distal ends.

3. The device of claim 2, wherein the bristles are provided on a pad of hook material of a hook and pile fastener.

4. The device of claim 1, wherein the brush is formed of a pad carrying the bristles and extends along the catheter longitudinally by about 0.5 to 1.5 cm.

5. The device of claim 4, wherein the pad extends substantially fully around a circumference of the catheter.

6. The device of claim 1, further comprising at least one marker means detectable externally of the duct, located adjacent the brush for guiding the brush to a selected location in the duct using an external means for detecting the marker.

7. The device of claim 6, wherein the marker means comprises a radio-opaque marker.

8. The device of claim 6, wherein the marker means comprises a pair of radio-opaque markers located adjacent the brush on opposite sides.

9. The device of claim 8, further comprising guide means for guiding the brush to a desired location by sliding the catheter over the guide means.

10. The device of claim 9, wherein the guide means comprises a guide wire longitudinally extending inside the catheter and having a blunt end extending beyond the distal end of the catheter.

11. The device of claim 1, further comprises a flexible material selected from the group consisting of nylon, polyethylene, polyurethane and polytetrafluoroethylene.

12. A device for performing simultaneous cytology and obtaining a scrape biopsy of tissue and cells at a stricture in a duct, comprising:

a flexible hollow catheter having a distal end for insertion into the duct and capable of being fed into the duct over a guide wire extending through the catheter to pass through the stricture, the catheter having an enlargement terminating at the distal end for expanding the duct;

a brush having semirigid bristles protruding substantially radially from the catheter and formed over a longitudinal distance adjacent the enlargement, the enlargement occupying an intermediate position between the brush and the distal end, the bristles being irregularly shaped bristles of a grasping portion of pad fastener material, disposed substantially around a full circumference of the catheter;

radio-opaque marker means near the brush for locating the brush by fluoroscopy;

a retractable sleeve movable between a covering position surrounding the brush and a retracted position exposing the brush;

wherein the sleeve is formed and arranged to be abuttable against the enlargement of the catheter for protecting the scraped cells collected on the brush during withdrawal of the catheter and sleeve combination from the duct.

13. A method for collecting cells and tissue from a selected area within a duct, comprising:

placing a guide wire in the duct such that the guide wire passes the selected area;

supplying a catheter, which catheter has a distal end, an enlargement terminating in the distal end, and a brush adjacent the enlargement, the enlargement occupying an intermediate position between the brush and the distal end;

inserting the catheter into the duct over the guide wire, the brush with semirigid bristles extending from the catheter, the bristles being irregularly shaped bristles of a hook portion of a hook and pile fastener, operable to capture the cells and tissue;

enlarging the duct to admit the brush by the enlargement of the catheter at the distal end of the catheter;

advancing the catheter to position the brush at the selected area;

alternately pushing and pulling the brush back and forth at the selected area, whereupon the cells and tissue accumulate in the bristles in the wake of the enlargement when the catheter is pushed; and, withdrawing the catheter and the brush from the duct wherein cells and tissues collected by brush are partly pushed by the enlargement.

14. The method of claim 13, further comprising enclosing at least the brush of the catheter in a sleeve at least when withdrawing the catheter and the brush from the duct.

15. The method of claim 13, further comprising locating the catheter by externally detecting at least one radio-opaque marker on the catheter adjacent the brush during at least one of said inserting, pushing and pulling and said withdrawing steps.

* * * * *